US011651491B2

(12) United States Patent
Siemionow et al.

(10) Patent No.: US 11,651,491 B2
(45) Date of Patent: May 16, 2023

(54) SYSTEM AND A METHOD FOR DETERMINING BRAIN AGE USING A NEURAL NETWORK

(71) Applicant: Inteneural Networks Inc., Chicago, IL (US)

(72) Inventors: Kris B. Siemionow, Chicago, IL (US); Paul Lewicki, Tulsa, OK (US); Marek Kraft, Poznan (PL); Michal Mikolajczak, Poznan (PL); Mikolaj Pawlak, Poznan (PL); Dominik Pieczynski, Tulce (PL)

(73) Assignee: INTENEURAL NETWORKS INC., Chicago, IL (US)

( * ) Notice: Subject to any disclaimer, the term of this patent is extended or adjusted under 35 U.S.C. 154(b) by 256 days.

(21) Appl. No.: 16/868,570

(22) Filed: May 7, 2020

(65) Prior Publication Data
US 2020/0357119 A1   Nov. 12, 2020

(30) Foreign Application Priority Data

May 9, 2019   (EP) .................................... 19173407

(51) Int. Cl.
*G06K 9/00* (2022.01)
*G06T 7/00* (2017.01)
(Continued)

(52) U.S. Cl.
CPC .......... *G06T 7/0014* (2013.01); *A61B 5/0042* (2013.01); *A61B 5/055* (2013.01);
(Continued)

(58) Field of Classification Search
CPC ......... G06T 7/0014; G06T 2207/10096; G06T 2207/20081; G06T 2207/20084; G06T 2207/30016; A61B 5/0042; A61B 5/055; A61B 5/7267; A61B 5/4064; A61B 2576/026; G01R 33/4806; G01R 33/5602; G01R 33/5608; G01R 33/56341;
(Continued)

(56) References Cited

U.S. PATENT DOCUMENTS

2016/0306936 A1* 10/2016 Mizobe ................. G16H 10/60
2020/0357119 A1* 11/2020 Siemionow .............. G06N 3/08

OTHER PUBLICATIONS

European Search Report of EP 19173407.8 dated Oct. 18, 2019.
(Continued)

*Primary Examiner* — Tom Y Lu
(74) *Attorney, Agent, or Firm* — Mark M. Friedman

(57) ABSTRACT

A method for determining a brain age, the method comprising the following: providing a brain age determining convolutional neural network (CNN) (200); training the CNN (200) to determine the brain age based on a plurality of sets of input data comprising magnetic resonance imaging (MRI) scans of a brain, the set comprising at least two types of MRI volumes, wherein the at least one type of brain tissue on the first type of the MRI volume is represented by a different contrast with respect to other tissues than on a second type of the MRI volume; and performing an inference process using the trained CNN (200) to determine the brain age based on the set of input data comprising magnetic resonance imaging (MRI) scans of a brain, the set comprising at least the two types of the MRI volumes as used for the training.

13 Claims, 6 Drawing Sheets

(51) Int. Cl.

| | |
|---|---|
| *G16H 50/30* | (2018.01) |
| *G16H 50/20* | (2018.01) |
| *G16H 30/40* | (2018.01) |
| *A61B 5/00* | (2006.01) |
| *A61B 5/055* | (2006.01) |
| *G01R 33/48* | (2006.01) |
| *G01R 33/56* | (2006.01) |
| *G01R 33/563* | (2006.01) |
| *G01R 33/565* | (2006.01) |
| *G06N 3/04* | (2023.01) |
| *G06N 3/08* | (2023.01) |

(52) U.S. Cl.
CPC ........ *A61B 5/7267* (2013.01); *G01R 33/4806* (2013.01); *G01R 33/5602* (2013.01); *G01R 33/5608* (2013.01); *G01R 33/56341* (2013.01); *G01R 33/56509* (2013.01); *G06N 3/04* (2013.01); *G06N 3/08* (2013.01); *G16H 30/40* (2018.01); *G16H 50/20* (2018.01); *G16H 50/30* (2018.01); *G06T 2207/10096* (2013.01); *G06T 2207/20081* (2013.01); *G06T 2207/20084* (2013.01); *G06T 2207/30016* (2013.01)

(58) Field of Classification Search
CPC ...... G01R 33/56509; G06N 3/04; G06N 3/08; G16H 30/40; G16H 50/20; G16H 50/30
See application file for complete search history.

(56) References Cited

OTHER PUBLICATIONS

Paul Herent et al: "Brain age prediction of healthy subjects on anatomic MRI with deep learning: going beyond with an "explainable AI" mindset", bioRxiv, (Sep. 10, 2018), XP055630058, DOI: 10.1101/413302 URL: https://www.biorxiv.org/content/biorxvi/early/2018/09/10/413302.full-text.pdf.

Tzu-Wei Huang et al: Age estimation from brain MRI images using deep learning:, 2017 IEEE 14th International Symposium on Biomedical Imaging (ISBI) IEEE Piscataway, NJ, USA, (Apr. 1, 2017), pp. 849-852, XP055630452, DOI: 10.1109/IBI.2017.7950650 ISBN: 978-1-5090-1172-8.

Saha Susmita et al: "Investigating Brain Age Deviation in Preterm Infants: A Deep Learning Approach", (Sep. 15, 2018) International Conference on Computer Analysis of Images and Patterns. CAIP 2017: Computer Analysis of Imagesand Patterns; [Lecture Notes in Computer Science; Lect. Notes Computer], Springer, Berlin, Heidelberg, pp. 87-96, XP047485710, ISBN: 978-3-642-17318-9.

Hongming Li et al: "Brain Age Prediction Based on Resting-State Functional Connectivity Patterns Using Convolutional Neural Networks", arxiv.org, Cornell University Library, 201 Olin Library Cornell University Ithica, NY 14853, (Jan. 12, 2018), XP081205976.

Bento Mariana et al: "Normal Brain Aging: Prediction of Age, Sex and White Matter Hyperintensities Using a MR Image-Based Machine Learning Technique", (Jun. 6, 2018), International Conference on Computer Analysis of Images and Patterns. CAIP 2017: Computer Analysis of Images and Patterns; [Lecture Notes in Computer Science; Lect. Notes Computer], Springer, Berlin, Heidelber, pp. 538-545, XP047476002, ISBN: 978-3-642-17318-9.

\* cited by examiner

SYSTEM AND A METHOD FOR DETERMINING BRAIN AGE USING A NEURAL NETWORK

TECHNICAL FIELD

The invention relates to determining brain age using a neural network.

BACKGROUND

The human brain changes across the adult lifespan. This process of brain aging occurs in parallel to a general decline in cognitive performance, known as cognitive aging. Although the changes associated with brain aging are not explicitly pathological, with increasing age comes increased risk of neurodegenerative disease and dementia (Abbott, 2011). However, brain disease can start at any age therefore the effects of aging on the brain vary greatly between individuals. Thus, advancing our understanding of brain aging and identifying biomarkers of the process is vital for improving the detection of early-stage neurodegeneration and predict cognitive decline related to age.

SUMMARY OF THE INVENTION

Neuroimaging-derived age predictions have been explored in the context of different brain diseases. By training models on healthy individuals, brain-based predictions of age can then be made in independent clinical samples. If 'brain-predicted age' is greater than an individual's chronological age, this may reflect some aberrant accumulation of brain injury. The degree of this 'added' brain aging can be simply quantified by subtracting chronological age from brain-predicted age.

The brain anatomy can be non-invasively visualized using magnetic resonance imaging (MRI). Various types of image contrasts, also called MRI sequences or MRI volumes, can be obtained to identify brain abnormalities. The most common volumes are T1-weighted, T2-weighted, and FLAIR (FLuid Attenuation Inversion Recovery) scans, although there are other methods to derive similar looking imaging using newer image acquisition methods like MAGIC that take advantage of other signal acquisition strategies (such as described in "Synthetic MRI for Clinical Neuroimaging: Results of the Magnetic Resonance image Compilation (MAGIC) Prospective, Multicenter, Multireader Trial" (by Tanenbaum L N et at, AJNR Am J Neuroradiol. 2017 June; 38(6):1103-1110). In general, the volumes obtainable by MRI imaging differ by the contrast in which different types of tissue are visualized.

A publication "Predicting brain age with deep learning from raw imaging data results in a reliable and heritable biomarker" (by James H Cole et al., arXiv: 1612.02572) discloses predicting brain age by a 3D CNN architecture that uses MRI volumes in a type of high-resolution T1-weighted MRI brain scans as inputs. The output to be predicted is a single scalar representing the biological age.

A publication "Brain age prediction of healthy subjects on anatomic MRI with deep learning: going beyond with an "explainable AI" mindset" (by Paul Herent et al., doi: http://dx.doi.org/10.1101/413302) discloses prediction of brain age using various machine learning and deep learning algorithms, where T1 weighted MRI scans were used as input.

The research attempts made so far were based on T1 weighted MRI volumes due to their broad accessibility and large age-span of the available samples. Although the types and resolution of volumes performed during patients' examinations vary a lot (depending on the reason for referral), T1-weighted volume is usually included in each of them. But the other types are also done for a reason and have their specific application: e.g. while T1 performs well in presenting overall brain anatomy structure, T2 works well in detection of white-matter pathologies, such as cysts or tumors by making them clearly visible in the scan, Flair can be successfully used in the evaluation of central nervous system disorder, etc. Because of that, a common practice during diagnosis by a doctor is to use information from these multiple, different types of MRI volumes in a complementary fashion. By focusing on only one type of them, current research attempts for automatic brain age assessment potentially limit the best achievable performance of system estimations.

There is disclosed herein certain embodiments of an improved, neural network-based system for determining brain age.

The invention relates to a method for determining a brain age, the method comprising, in certain embodiments, the following: providing a brain age determining convolutional neural network (CNN); training the CNN to determine the brain age based on a plurality of sets of input data comprising magnetic resonance imaging scans of a brain, the set comprising at least two types of MRI volumes, wherein the at least one type of brain tissue on the first type of MRI volume is represented by a different contrast with respect to other tissues than on a second type of the MRI volume; and performing an inference process using the trained CNN to determine the brain age based on the set of input data comprising magnetic resonance imaging scans of a brain, the set comprising at least the two types of the MRI volumes as used for the training.

The first type of the MRI volumes may comprise T1-weighted scans and the second type of the MRI volumes comprises T2-weighted scans.

The set of input data may further comprise Flair scans.
The set of input data may further comprise DWI scans.
The MRI volumes may be obtained by synthetic MRI.
The set of input data may further comprise scans of brain with contrast addition.
The set of input data may further comprise patient metadata that include at least one of: age and sex.

The method may further comprise: determining a brain map comprising a plurality of areas; selecting at least one area of the brain map and occluding the input data scans within the selected area; using the trained CNN, determining the brain age based on the set of input data comprising the occluded area; comparing the brain age determined for the occluded data and initial data and determining whether the area is significant for the determined brain age; and presenting indication of which areas are significant for the determined brain age.

There is also disclosed a computer-implemented system, comprising: at least one nontransitory processor-readable storage medium that stores at least one of processor-executable instructions or data; and at least one processor communicably coupled to the at least one nontransitory processor-readable storage medium, wherein that at least one processor is configured to: receive a set of input data comprising magnetic resonance imaging scans of a brain, the set comprising at least two types of MRI volumes, wherein the at least one type of brain tissue on the first type of the MRI volume is represented by a different contrast with respect to other tissues than on a second type of the MRI volume; and perform an inference process using a trained brain age determining convolutional neural network (CNN) that accepts the input data as the input and outputs the brain age depending on the input data.

The system and method for determining brain age, in certain embodiments, leverages information from not only T1, but also other, complementary volumes (and optionally patient's metadata, such as handedness, sex, demographics, etc.)—thereby replicating in a better way a real-world scenario.

BRIEF DESCRIPTION OF DRAWINGS

Various embodiments are herein described, by ay of example only, with reference to the accompanying drawings, wherein.

DETAILED DESCRIPTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Figure 1:
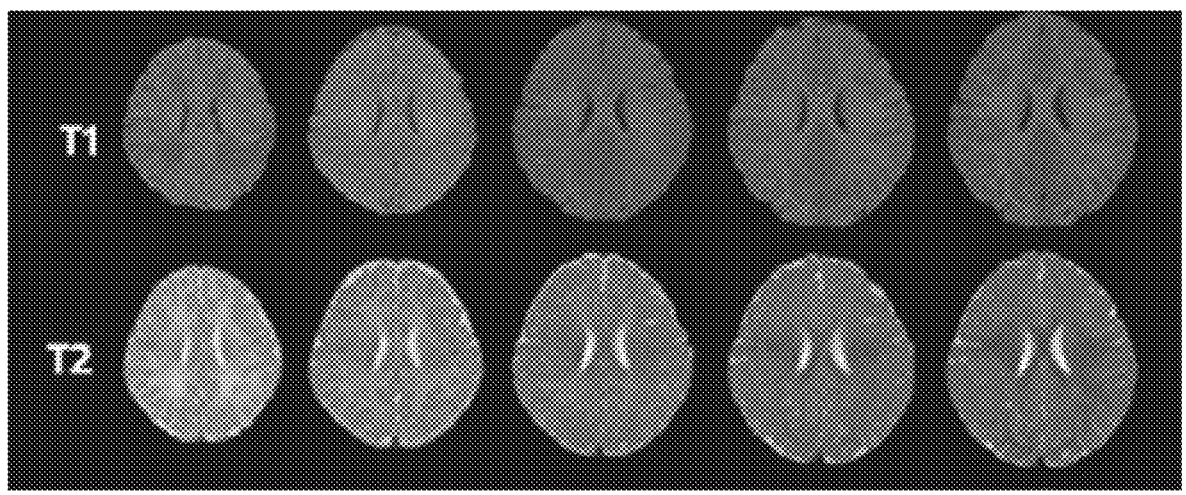
FIG. 1 shows examples of axial cross-sections of input volumes of T1 and T2 volumes.

The system as presented herein uses at least two types of MRI volumes as input volumes, as shown in FIG. 1, such as:

T1-weighted volumes that are used to differentiate anatomical structures mainly on the basis of T1-weighted values; i.e. the scanning parameters are set (short TR/short TE) to minimize T2 relaxation effects. Tissues with high-fat content (e.g. white matter) appear bright and compartments filled with water (e.g. CSF) appears dark. This is good for demonstrating anatomy. For example, T1-weighted volumes can be made for TR equal to 500 milliseconds and TE equal to 14 milliseconds.

T2-weighted volumes that are used to differentiate anatomical structures mainly on the basis of T2 values; i.e. the scanning parameters are set (long TR/long TE) to minimize T1 relaxation effects. Compartments filled with water (e.g. CSF compartments) appear bright and tissues with high fat content (e.g. white matter) appear dark. This is good for demonstrating pathology since most (not all) lesions are associated with an increase in water content. For example, T2-weighted volumes can be made for TR equal to 4000 milliseconds and TE equal to 90 milliseconds.

Furthermore, additional input volumes can be optionally used, such as:

Flair volumes, for example made for TR equal to 9000 milliseconds and TE equal to 114 milliseconds;

Diffusion weighted volumes that measure microscopic water molecule movement biological system. They are often used for detection of ischemic stroke and white matter lesions resulting from cerebrovascular disease;

variations of the above-mentioned, volumes with contrast addition.

In general, the at least two types of MRI input volumes shall differ in that at least one type of brain tissue on the first type of the MRI volume is represented by a different contrast with respect to other tissues than on a second type of the MRI volume.

The term "volume" as used herein refers to a series of images corresponding to a 3D representation of the brain.

Due to their described characteristics, each of these types of MRI contrast allow experts to notice and diagnose different kind of structures and/or pathologies, and are used in complementary fashion during potential diagnosis.

In the recent prior art publications on the topic, as described herein, the "brain age" biomarker, regardless of the algorithm of calculation used, the input comes from T1 volume. The reason is that in publicly available public datasets IXI, INDI) this type of volume is almost always included, which unfortunately cannot be said for other types of volumes.

However, for today's examinations in a hospital environment it is usually the case that most patients receive a scan resulting in actually a set of volumes—not limited to only T1, but containing also already mentioned T2, and other ones such as FLAIR, DWI, or variations of these with contrast addition. The set of volume types made for individual examinations varies, depending on the reason for the referral still, T1 and T2 MRI volumes are almost always included. Their overall availability is also one of the greatest assets.

When designing the system as presented herein it turned out that both T1-weighted and T2-weighted contrasts complement each other. Such approach reflects the majority of routine head examinations performed for clinical applications.

Figure 2:
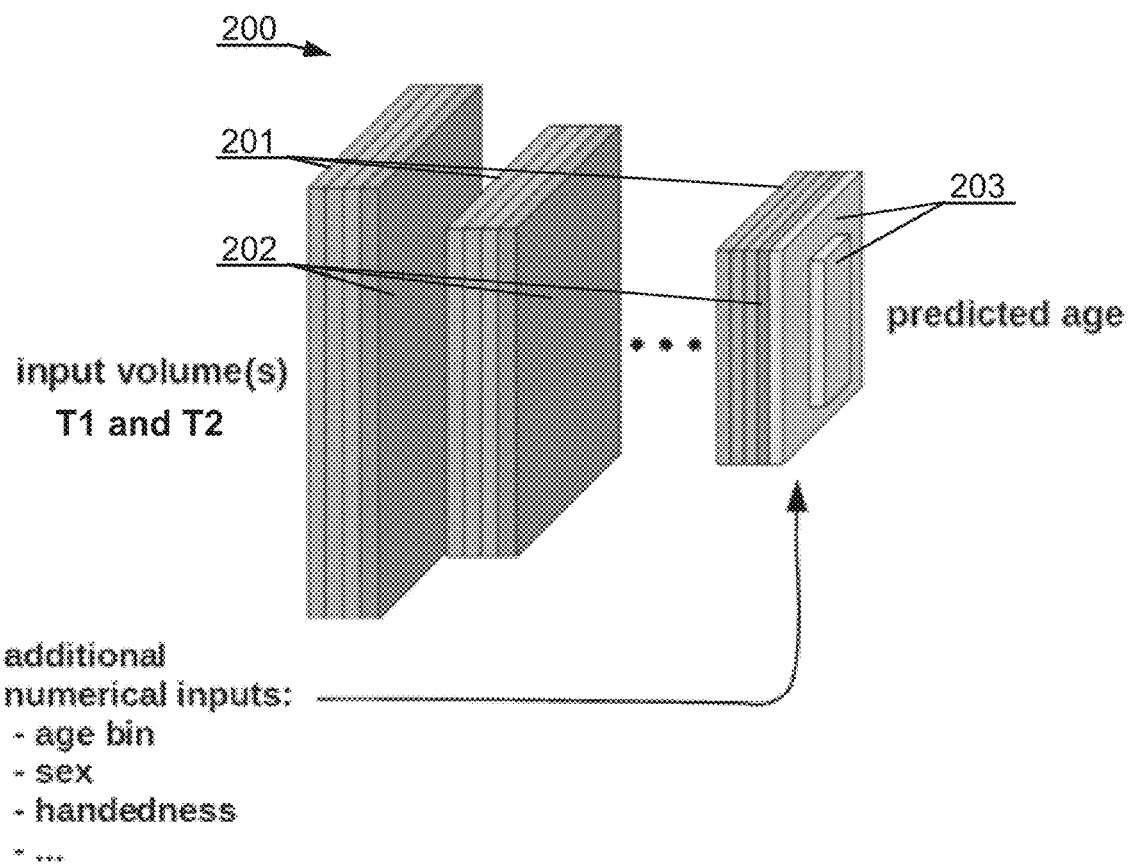
FIG. 2 shows a brain age determining convolutional neural network (CNN) architecture in accordance one embodiment.

FIG. 2 shows a brain age determining convolutional neural network (CNN) architecture 200 used to determine the brain age. The network has a contracting path comprising 3D convolutional layers 201, pooling layers 202 and dense layers 203. Each convolutional layer 202 has a plurality of filters (for example, from 16 to 512 filters). Convolutions may be of the regular kind or dilated convolutions. A different stride of $S_C$ (for example: 1, 2, 4 or 8) can be set for each convolutional layer 201. The 3D maximum pooling layers 202 may have optional added dropout or other regularization. A different stride of $S_{MP}$ (for example, 1, 2, 4 or 8) can be set for each pooling layer 202. The dense layers 203 may have an optionally added dropout or other regularization.

The network is configured to accept as a primary input a set of T1-weighted and T2-weighted volumes of the brain to be analyzed, preferably provided as a multichannel 3D volume. In addition, the primary input may further comprise volumes of other types, such as dark-fluid T2-weighted or diffusion weighted volumes or their variations with contrast addition.

The network can be further configured to accept as an additional input: supplemental, non-image information, such as gender, age group, handedness etc. of the patient whose brain image is analyzed. These additional inputs are preferably provided to the layer or layers 203 performing the final prediction, such as dense layers or global average pooling layers. In particular, the additional input may be classified in bins including a plurality of values, for example age can be classified in bins such as bins for ages 0-10; 10-20; 20-30 etc.

The network is configured to provide, as output, a determined brain age, based on at least the T1-weighted and T2-weighted volumes of the brain provided as the primary input data.

Figure 3:
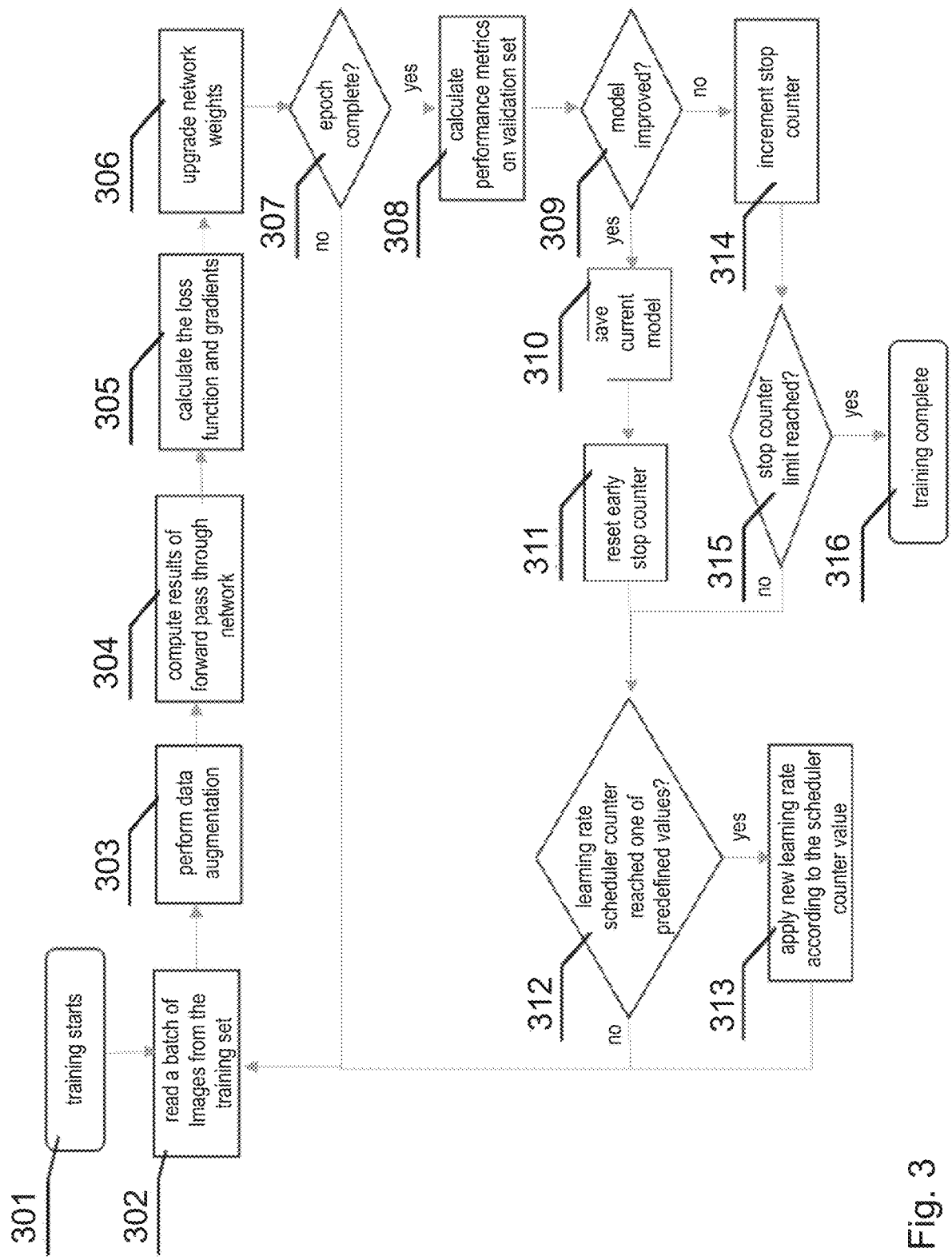
FIG. 3 is a flow chart that shows a training process of the brain age determining CNN in accordance with one embodiment.

The training process of the brain age determining CNN 200 is carried out as shown in FIG. 3. The objective of the training for the CNN 200 is to tune the parameters of the CNN 200, so that the network is able to determine the brain age. The training database may be split into a training set used to train the model, a validation set used to quantify the quality of the model, and a test set. The training database may comprise a plurality of sets of at least the T1-weighted and T2-weighted scans of healthy individuals with their biological age. At least some of the sets may include other scans (e.g. Flair, DWI) or additional data (e.g. age, sex, handedness).

The training starts at 301. At 302, batches of training volumes (at least the T1-weighted and T2-weighted scans) are read from the training set, for example one batch at a time.

At 303 the original scans can be augmented. Data augmentation is performed on these scans to make the training set more diverse. The input and output pair of three dimensional volumes is subjected to the same combination of transformations.

At 304, the original 3D volumes and the augmented 3D volumes are then passed through the layers of the CNN in a standard forward pass. The forward pass returns the results, which are then used to calculate at 305 the value of the loss function (i.e., the difference between the desired output and the output computed by the CNN). The difference can be expressed using a similarity metric (e.g., mean squared error, mean average error, categorical cross-entropy, or another metric).

At 306, weights are updated as per the specified optimizer and optimizer learning rate. The loss may be calculated using a per-pixel cross-entropy loss function and the Adam update rule.

The loss is also back-propagated through the network, and the gradients are computed. Based on the gradient values, the network weights are updated. The process, beginning with the 3D volumes batch read, is repeated continuously until an end of the training session is reached at 307.

Then, at 308, in accordance with certain embodiments, the performance metrics are calculated using a validation dataset—which is not explicitly used in training. This is done in order to check at 309 whether not the model has improved. If it is not the case, the early stop counter is incremented by one at 314, as long as its value has not reached a predefined maximum number of epochs at 315. The training process continues until there is no further improvement obtained at 316. Then the model is saved at 310 for further use, and the early stop counter is reset at 311. As the final step in a session, learning rate scheduling can be applied. The session at which the rate is to be changed are predefined. Once one of the session numbers is reached at 312, the learning rate is set to one associated with this specific session number at 313.

Once the training process is complete, the network can be used for inference (i.e., utilizing a trained model for autonomous determination of the brain age). The model can be saved and reused, training doesn't need to be performed before each use.

In other words, the neural network adjusts its internal parameters, which include the weights in the internal convolutional layers of the dimensions W×H×D (they include 3D convolutional kernels), which denote the width and height and depth, respectively, with W, H and D being positive integers and the weights of the additional fully connected layers. During training, the network repeatedly performs the following steps in certain embodiments:

the step of determining the age based in the input MRI imaging data, the computation of the difference between the actual age (as given in the training data) and the determined age The update of weights according to the gradient back-propagation method based on the steepest descent gradient algorithm or one of its variants (Adam, Nadam, adagrad, . . . )

Doing so, the network adjusts its parameters and improves its predictions over time. During training, the following means of improving the training accuracy can be used in certain embodiments:

Learning rate scheduling

Early stopping

Regularization by dropout

L2 regularization

Data augmentation (by random volume rotations, intensity changes, noise introduction, affine transformations etc.)

The training process includes periodic check of the brain age determination accuracy a held out input data set (the validation set) not included in the training data. If the check reveals that the accuracy on the validation set is better than the one achieved during the previous check, the complete neural network weights are stored for further use. The early stopping function may terminate the training if there is no improvement observed during the last checks. Otherwise, the training is terminated after a predefined number of steps.

The approach presented herein has the advantage that it does not require significant pre-processing of input data. This makes the system less complex.

The input data is normalized from the raw MRI data to a range from 0 . . . 1. Preferably, before the normalization, the extreme top and bottom values may be clipped (discarded), to get rid of outlying values.

Figure 4:
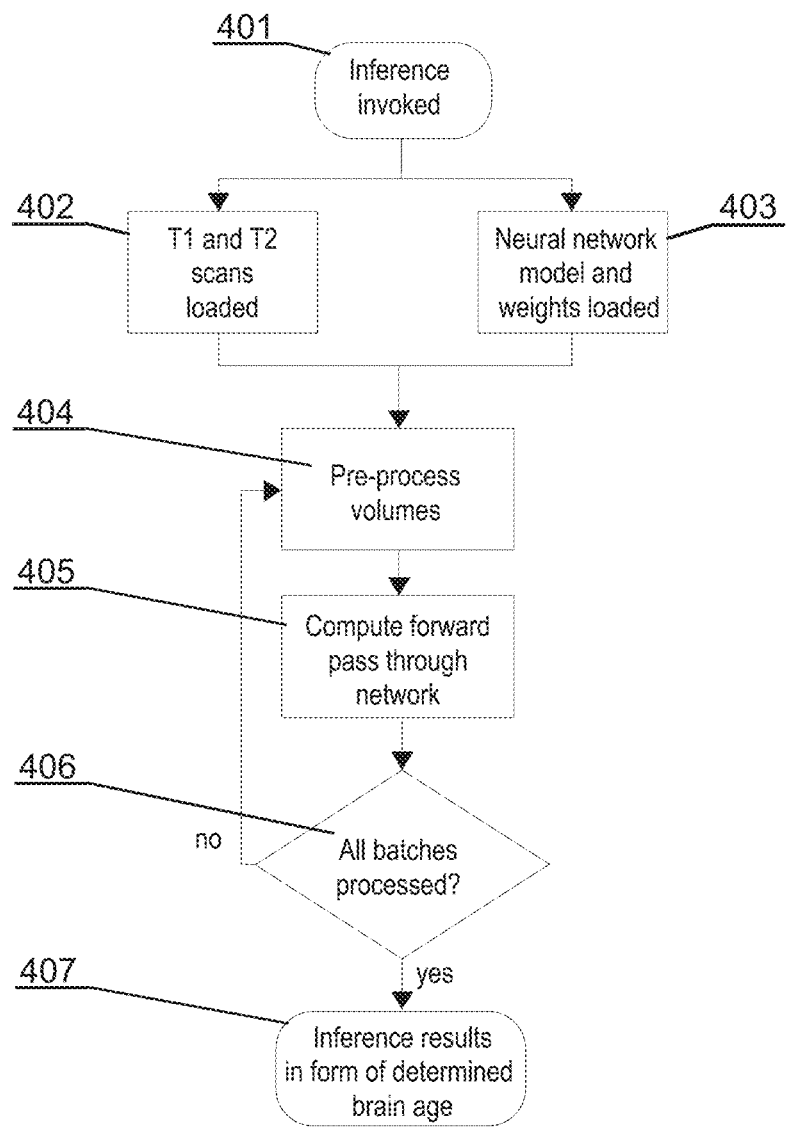
FIG. 4 is a flow chart that shows an inference process for the brain age determining CNN in accordance with one embodiment.

FIG. 4 shows a flowchart of an inference process for the brain age determining CNN 200.

After inference is invoked at 401, a set of at least the T1-weighted and T2-weighted scans and optionally other scans (e.g. Flair, DWI) or additional data (e.g. age, sex, handedness) is loaded at 402 and the CNN 200 and its weights are loaded at 403.

At 404, the input volume is preprocessed (e.g., normalized, cropped, etc.) using the same parameters that were utilized during training.

At 405, a forward pass through the CNN 200 is computed.

At 406, if not all batches have been processed, a new batch is added to the processing pipeline until inference has been performed at all input volumes.

Finally, at 407, the inference results are saved and the output is provided as a determined brain age.

In case the determined brain age deviates from the patient's age, then apart from simply presenting the result of the inference as a value of the determined brain age, a further process may be performed to determine which areas of the brain contributed to the result. In that case, the result of that process may be a message such as 'The area that contributed to the decision is X and Y, which may mean the patient is susceptible to A, B and C'.

Figure 5:
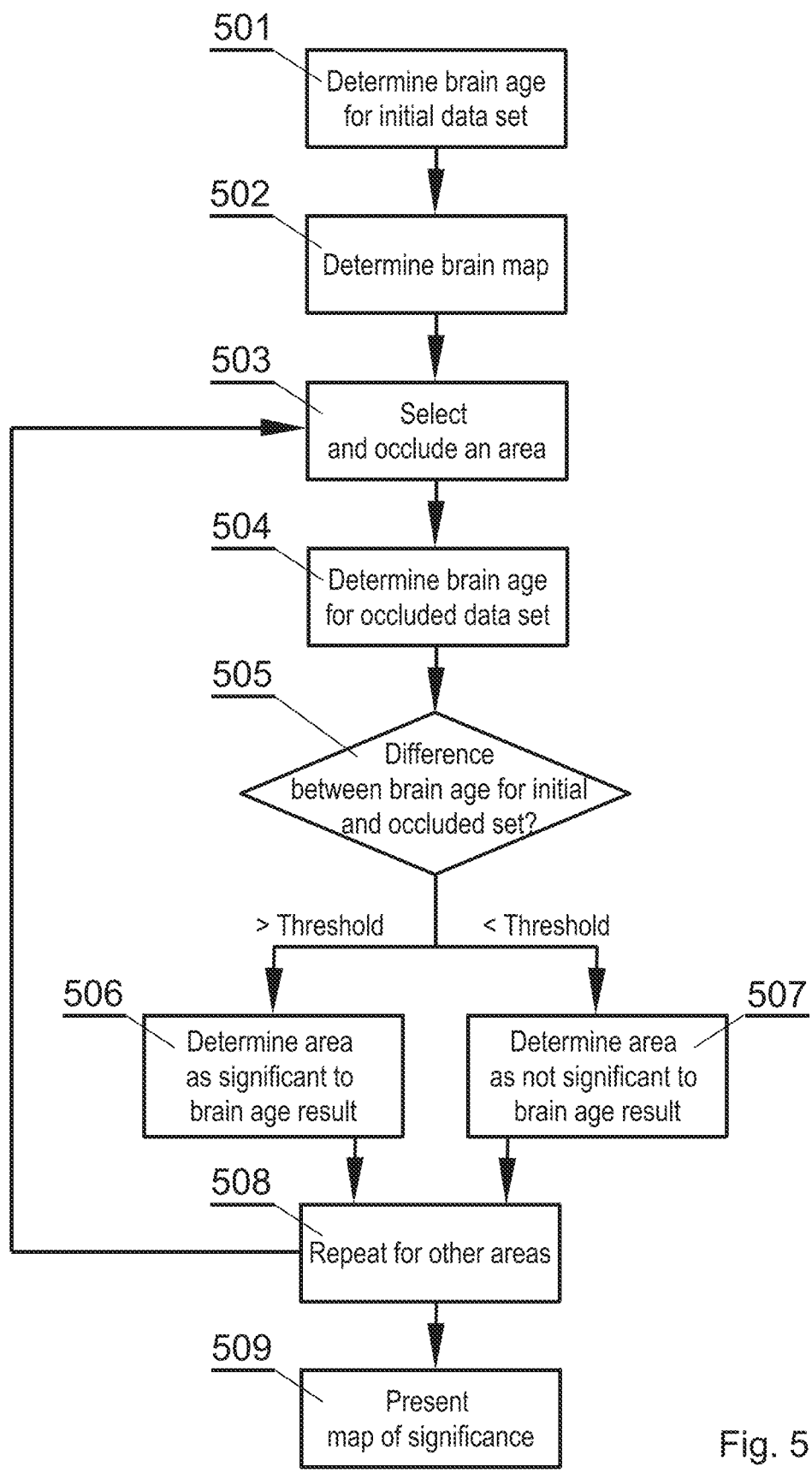
FIG. 5 is a flow chart that shows a procedure for determining the areas that the determined brain age in accordance with one embodiment.

FIG. 5 shows a procedure for determining the areas that contribute to the determined brain age. The process is based on the idea of partial occlusion of areas of the brain.

Figure 6A:
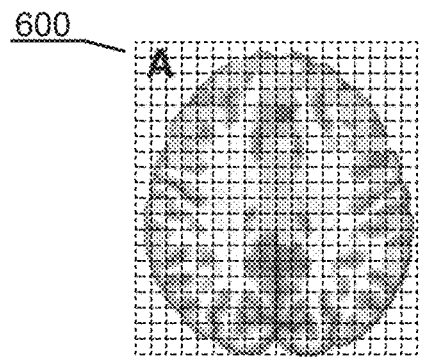
FIG. 6A shows various areas of a brain with a map, in accordance with one embodiment.
Figure 6B:
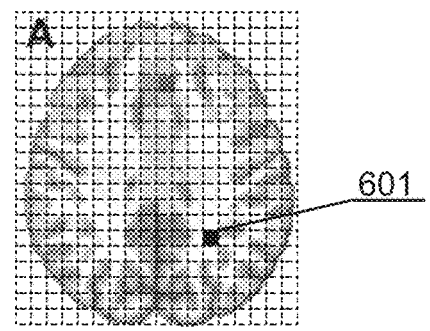
FIG. 6B shows a map with an occluded area in accordance with one embodiment.
Figure 6C:
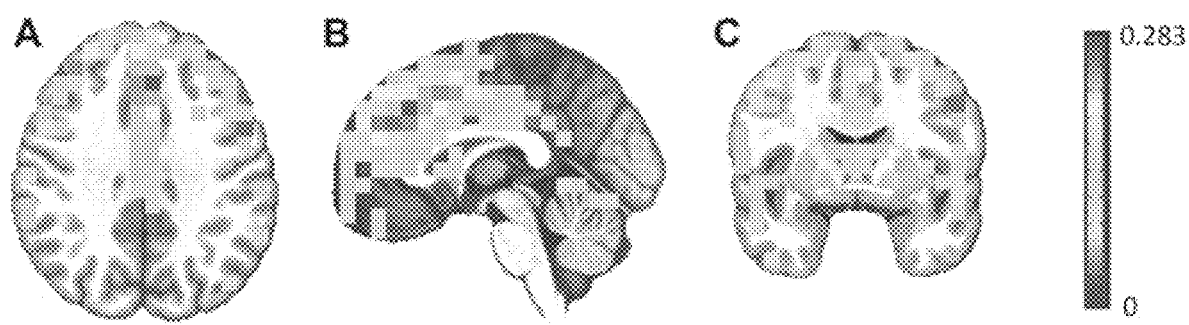
FIG. 6C shows significance of each analyzed area in accordance with one embodiment.

First, at 501, inference result is determined by the trained CNN 200 for the original set of input data, including at least the T1-weighted and T2-weighted volumes (and possibly other imaging data) as the initially determined brain age. Next, at 502, a map is determined, such as shown in FIG. 6A, that defines various areas of the brain. The map 600 may have a form of a rectangular grid or a grid with other, even irregular, shape of cells 601. Next, at 503, at least one of the areas 601 of the map is occluded in the original input scans (e.g. data related to this area is zeroed). FIG. 6B shows an image with one occluded area 601. The set of occluded scans is input at 504 to the CNN 200 and the inference result (i.e. the determined brain age for the occluded set) is compared at 505 with the initially determined brain age. If the difference is significant at 506, i.e. higher than a predetermined threshold, that occluded area is marked as an area that is significant for the determination of the brain age. If not, that occluded area is marked as not significant at 507. More threshold levels may be also defined, for determining different levels of significance. In other words, the areas which cause the greatest error when occluded are the ones that are most important when calling the final value for determination of the brain age. The steps 503-507 are repeated at 508 for different areas 601. In each iteration, a single area may be occluded or a plurality of areas may be occluded. Various overlapping areas may be processed in successive iterations and the results indicating the significance of particular areas may be aggregated to determine a final result. After a number of the areas 601 of the map 600 are analyzed, the result indicating a significance of each analyzed area is presented at 509, such as shown in FIG. 6C. For example, each area indicated as significant may be highlighted by a color, the intensity or shade of which indicates the level of significance.

The procedure shown in FIG. 5 allows one to determine, which parts of the brain were responsible for the specific prediction of the brain age. Consequently, localizing the brain part that influenced a prediction of the brain age that significantly differs from the biological age may directly indicate where to look for abnormalities and degenerations, which in turn enables more informed and faster diagnosis.

Landmark based identification of pathological processes can enrich the analysis through rapid quantification of brain structure shape. For example, ventricular width is correlated with normal, regular aging, but might also indicate a possibility of Alzheimer's or hydrocephalus. Contribution from the hippocampal region might also indicate some Alzheimer's probability (such as described in "Age-related changes of lateral ventricular width and periventricular white matter in the human brain: a diffusion tensor imaging study" (by Yong Hyun Kwon et al., Neural Regen Res. 2014 May 1; 9(9): 986-989)). Linking to grey matter/white matter regions or the regions with high grey matter concentration/gyrification might be an indicator of Alzheimer's and multiple sclerosis (such as described in "Multiple sclerosis in 2018: new therapies and biomarkers" (by Olga Ciccarelli, the Lancet, Neurology, 2018 Round-up| Volume 18, ISSUE 1, P 10-12, Jan. 1, 2019). Placing the prediction contribution indicators in these regions while signaling an unusually high brain age might be an early indicator of those conditions.

Figure 7:
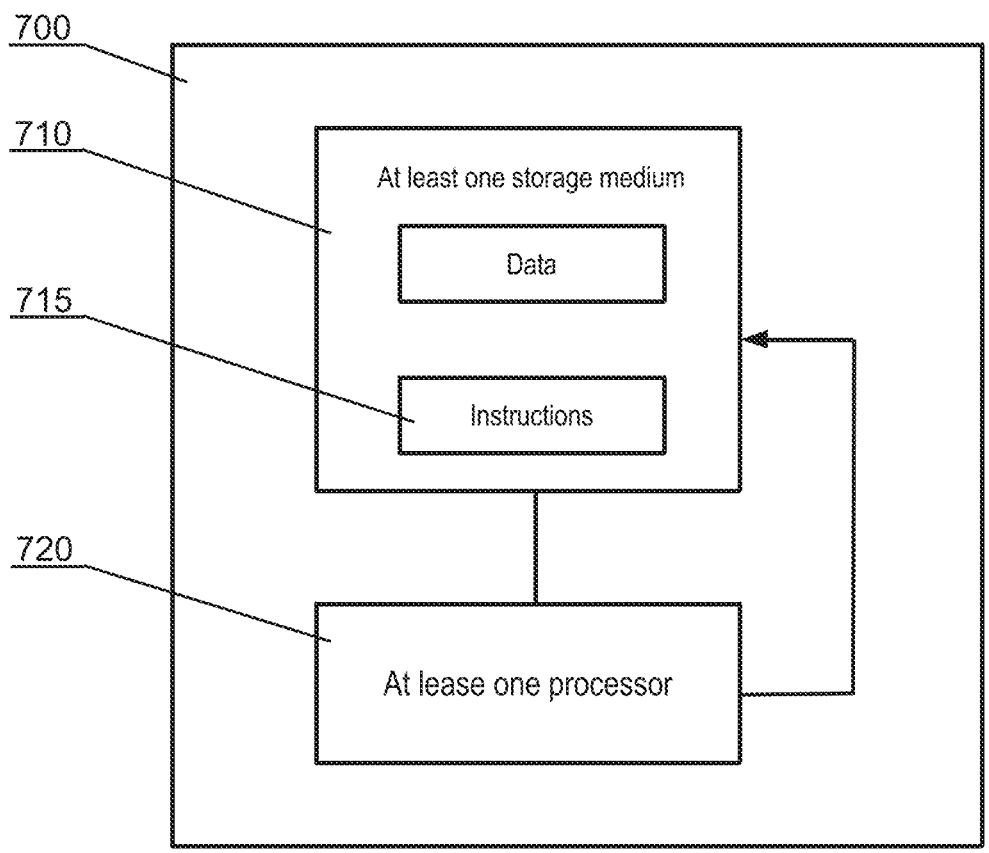
FIG. 7 is a schematic that shows a computer-implemented system in accordance with one embodiment.

The functionality described herein can be implemented in a computer-implemented system 700, such as shown in FIG. 7. The system may include at least one non-transitory processor-readable storage medium that stores at least one of processor-executable instructions or data and at least one processor communicably coupled to the at least one non-transitory processor-readable storage medium. The at least one processor is configured to perform the steps of any of the methods presented herein.

The computer-implemented system 700, for example a machine-learning system, may include at least one non-transitory processor-readable storage medium 710 that stores at least one of processor-executable instructions 715 or data; and at least one processor 720 communicably coupled to the at least one non-transitory processor-readable storage medium 710. The at least one processor 720 may be configured to (by executing the instructions 715) to perform the steps of any of the methods of FIG. 3-5.

Although the invention is presented in the drawings and the description and in relation to its embodiments, these embodiments do not restrict nor limit the presented invention. It is therefore evident that changes, which come within the meaning and range of equivalency of the essence of the invention, may be made. The presented embodiments are therefore to be considered in all aspects as illustrative and not restrictive. According to the abovementioned, the scope of the invention is not restricted to the presented embodiments but is indicated by the appended claims.

What is claimed is:

1. A method for determining a brain age, the method comprising the following:
   (a) providing a brain age determining convolutional neural network (CNN);
   (b) training the CNN to determine the brain age based on a plurality of sets of input data comprising magnetic resonance imaging (MRI) scans of a brain, each set of the plurality of sets comprising at least two types of MRI volumes, wherein the at least one type of brain tissue on the first type of the MRI volume is represented by a different contrast with respect to other tissues than on a second type of the MRI volume; and
   (c) performing an inference process using the trained CNN to determine the brain age based on the set of input data comprising magnetic resonance imaging (MRI) scans of a brain, the set comprising at least the two types of the MRI volumes as used for the training.

2. The method according to claim 1, wherein the first type of the MRI volumes comprises T1-weighted scans and the second type of the MRI volumes comprises T2-weighted scans.

3. The method according to claim 2, further comprising:
   determining a brain map comprising a plurality of areas;
   selecting at least one area of the brain map and occluding the input data scans within the selected area;
   using the trained CNN, determining the brain age based on the set of input data comprising the occluded area;
   comparing the brain age determined for the occluded data and initial data and determining whether the area is significant for the determined brain age; and
   presenting indication of which areas are significant for the determined brain age.

4. The method according to claim 1, wherein the set of input data further comprises Flair scans.

5. The method according to claim 4, further comprising:
determining a brain map comprising a plurality of areas;
selecting at least one area of the brain map and occluding the input data scans within the selected area;
using the trained CNN, determining the brain age based on the set of input data comprising the occluded area;
comparing the brain age determined for the occluded data and initial data and determining whether the area is significant for the determined brain age; and
presenting indication of which areas are significant for the determined brain age.

6. The method according to claim 1, wherein the set of input data further comprises DWI scans.

7. The method according to claim 6, further comprising:
determining a brain map comprising a plurality of areas;
selecting at least one area of the brain map and occluding the input data scans within the selected area;
using the trained CNN, determining the brain age based on the set of input data comprising the occluded area;
comparing the brain age determined for the occluded data and initial data and determining whether the area is significant for the determined brain age; and
presenting indication of which areas are significant for the determined brain age.

8. The method according to claim 1, wherein the MRI volumes are obtained by synthetic MRI.

9. The method according to claim 8, further comprising:
determining a brain map comprising a plurality of areas;
selecting at least one area of the brain map and occluding the input data scans within the selected area;
using the trained CNN, determining the brain age based on the set of input data comprising the occluded area;
comparing the brain age determined for the occluded data and initial data and determining whether the area is significant for the determined brain age; and
presenting indication of which areas are significant for the determined brain age.

10. The method according to claim 1, wherein the set of input data further comprises scans of brain with contrast addition.

11. The method according to claim 1, wherein the set of input data further comprises patient metadata that include at least one of: age and sex.

12. The method according to claim 1, further comprising:
determining a brain map comprising a plurality of areas;
selecting at least one area of the brain map and occluding the input data scans within the selected area;
using the trained CNN, determining the brain age based on the set of input data comprising the occluded area;
comparing the brain age determined for the occluded data and initial data and determining whether the area is significant for the determined brain age; and
presenting indication of which areas are significant for the determined brain age.

13. A computer-implemented system, comprising:
at least one nontransitory processor-readable storage medium that stores at least one of processor-executable instructions or data; and
at least one processor communicably coupled to the at least one nontransitory processor-readable storage medium, wherein the at least one processor is configured to:
(a) receive a set of input data comprising magnetic resonance imaging (MRI) scans of a brain, each set of the plurality of sets comprising at least two types of MRI volumes, wherein the at least one type of brain tissue on the first type of the MRI volume is represented by a different contrast with respect to other tissues than on a second type of the MRI volume; and
(b) perform an inference process using a trained brain age determining convolutional neural network (CNN) that accepts the input data as the input and outputs the brain age depending on the input data.

* * * * *